United States Patent [19]

Treadwell et al.

[11] Patent Number: 5,284,155
[45] Date of Patent: Feb. 8, 1994

[54] CARTILAGE DEGRADATION ASSAY SYSTEM

[75] Inventors: Benjamin V. Treadwell, Boston; Hieu T. Ball, Somerville; Henry T. Mankin, Brookline, all of Mass.

[73] Assignee: The General Hospital Corporation, Boston, Mass.

[21] Appl. No.: 802,892

[22] Filed: Dec. 6, 1991

[51] Int. Cl.$^5$ .................. A61B 10/00; A61B 5/00; A61F 2/28
[52] U.S. Cl. ...................... 128/749; 128/760; 623/16
[58] Field of Search ............ 128/749, 760; 623/16; 424/489, 491, 493, 499, 520

[56] References Cited

U.S. PATENT DOCUMENTS

| | | | |
|---|---|---|---|
| Re. 28,093 | 7/1974 | Balassa et al. | 424/95 |
| 3,476,855 | 11/1969 | Balassa et al. | 424/95 |
| 3,772,432 | 11/1973 | Balassa et al. | 424/95 |
| 4,473,551 | 9/1984 | Schinitsky | 424/548 |
| 4,642,120 | 2/1987 | Nevo et al. | 623/16 |
| 4,656,137 | 4/1987 | Balassa | 424/548 |

FOREIGN PATENT DOCUMENTS 0774546 10/1980 U.S.S.R. ................ 128/760

OTHER PUBLICATIONS

Dingle et al., 1979, Biochem. J. 184:177–180.
Treadwell et al., 1986, Archives of Biochem. and Biophys. 251:715–723.

*Primary Examiner*—Randall L. Green
*Assistant Examiner*—Dinh X. Nguyen
*Attorney, Agent, or Firm*—Fish & Richardson

[57] ABSTRACT

Methods for diagnosing and monitoring arthritic disease with an inflammatory joint component in a mammal are described. The methods comprise (a) obtaining a sample of powdered cartilage or synovial fluid from the mammal, (b) mixing the sample with powdered cartilage, or protein that is detectably labeled, (c) determining the amount of label released from the powdered cartilage or protein, the amount being indicative of the level of protease activity, and (d) comparing the level to a standard, or to the level obtained from a sample taken at another time point, wherein the level is an indication of the presence or progression of the arthritic disease.

10 Claims, No Drawings

CARTILAGE DEGRADATION ASSAY SYSTEM

BACKGROUND OF THE INVENTION

The field of the invention is cartilage degradation.

Hyaline cartilage, which covers the articular ends of the bones, contains primarily proteoglycans in its intracellular matrix. The breakdown of these proteoglycans in arthritic diseases, such as osteoarthritis and rheumatoid arthritis, leads to loss of the capacity of cartilage to resist wear. Proteoglycan aggregate, which has a high molecular weight, comprises three portions - namely, the proteoglycan subunit, hyaluronic acid, and link protein. The proteoglycan subunit comprises chondroitin sulfate and keratan sulfate chains, which are attached to a protein core. Chondroitin sulfate, keratan sulfate and hyaluronic acid are glycosaminoglycans, polysaccharides comprising two different sugar residues that alternate regularly in the polysaccharide chain.

The arthritides, for example osteoarthritis, are not a single nosologic entity, but rather a group of disorders that have in common the mechanical destruction of a joint. The biochemical changes in osteoarthritis primarily involve proteoglycans. There is a decrease in proteoglycan content and aggregation, as well as a decrease in the chain length in the glycosaminoglycans. Compared to the level in normal articular cartilage, keratan sulphate is decreased and chondroitin sulfate is increased. In the early stages of osteoarthritis, synthesis of matrix by chondrocytes is augmented, presumably as a reparative action As the osteoarthritis progresses, protein synthesis declines, suggesting that the cell reaches a point where it fails to respond to reparative stimuli. Levels of proteases in the cartilage increase, and active proteolytic enzymes not normally found in cartilage can be detected.

Rheumatoid arthritis is a systemic, chronic, inflammatory disease that involves the joints and, like osteoarthritis, comprises a heterogeneous group of disorders. While many of the pathological changes in rheumatoid arthritis are distinct from those in osteoarthritis, a common feature is degradation of cartilage, particularly loss of proteoglycans. Drugs used to treat rheumatoid arthritis primarily suppress the inflammatory processes that contribute to the pathology.

At present, there is no specific treatment for arresting degradation of cartilage in humans with arthritic diseases.

SUMMARY OF THE INVENTION

In general, the invention features a powdered cartilage assay system designed to test the action of any factor (inhibitors and activators) which might affect cartilage degradation. The invention permits the sort of large scale testing of factors which is logistically unfeasible in existing assay systems.

Accordingly, the invention features a method for assaying the ability of a test substance to promote or inhibit cartilage degradation in a mammal; the method involves a) mixing the test substance with powdered cartilage which is suspended in liquid, wherein the proteoglycan moieties in the matrix of the cartilage are labelled by incubating the cartilage, prior to powder formation, with a detectable label, and then b) detecting the release of label from the cartilage as an indication of promotion or inhibition of degradation of the cartilage by the test substance.

The invention also features a method for assaying the ability of a test substance to promote or inhibit cartilage degradation in a mammal; the method involves a) mixing the test substance with powdered cartilage which is suspended in liquid, in the presence of a dye capable of binding to glycosaminoglycan moieties released from the cartilage and undergoing a color change when so bound, and then b) detecting such detectable change as a measure of promotion or inhibition of degradation of the cartilage by the test substance.

Also contained within the invention is a method for testing synovial fluid for the presence of materials that affect cartilage degradation. Such testing is accomplished either in the presence or absence of cartilage.

In preferred embodiments, the invention features a powdered assay system which is available as a kit, wherein the kit is used to carry out the above methods, as well as to expedite the discovery of proteases and other factors that exist in the articular cartilage matrix, in synovial fluid, bronchoalveolar lavage, serum, urine and blister exudate from a mammal.

The assay of the invention can be implemented as a diagnostic tool to determine the presence of arthritic disease with an inflammatory joint component in a mammal, or to measure activators and inhibitors of cartilage degradation in the synovial fluid or cartilage of a mammal with this arthritic disease.

The assay of the invention can also be implemented as a tool for monitoring the progression of arthritic disease with an inflammatory joint component in a mammal, wherein synovial fluid or cartilage obtained from the mammal can be tested at two or more time points for proteases and other factors that affect cartilage degradation, and the results obtained at the time points can be compared.

In yet other preferred embodiments, the arthritic disease in the mammal is osteoarthritis or rheumatoid arthritis.

Other features and advantages of the invention will be apparent from the following description of the preferred embodiments thereof, and from the claims.

DETAILED DESCRIPTION

The powdered cartilage assay system involves the steps of preparation of powdered cartilage and the use of this cartilage to test for, or assay for, substances that affect degradation of the cartilage. Methods for the preparation of powdered cartilage and its use as a component in the assay system are described below.

Powdered Cartilage. Bovine cartilage from radiocarpal joints of calves was resected. The cartilage chips were thoroughly washed in phosphate buffered saline (PBS, pH 7.4), placed in Dulbecco's modified Eagle medium (DMEM) and labelled with [$^{35}$S]O$_4$ for 48–72 hours at 3720 C. in an atmosphere of 95% air, 5% CO$_2$. After incubation, the cartilage was pulverized using a liquid nitrogen Spex TM Mill in order to preserve cartilage matrix components (e.g., enzymes, collagen, etc.). The resulting cartilage powder was then filtered through a Bellco TM tissue homogenizing sieve (size 20 Mesh, 860 micron opening size) to remove unusually large pieces of powder that were not properly pulverized. The powder was thoroughly washed several times with TBS (Tris-Cl buffered saline, 20 mM Tris, 150 mM NaCl, pH 7.4) to remove any non-bound soluble enzymes liberated during pulverization. Finally, the powder was lyophilized to dryness and stored at −40° C.

The Powdered Cartilage Assay. An enzyme examined with the new assay system was stromelysin, a metalloprotease. The metalloproteases are suspected of playing an important role in the catalytic cascade of activity responsible for cartilage degradation in degenerative diseases, such as osteoarthritis. Many researchers believe that latent metalloproteases are present in the cartilage matrix in a soluble form, where they may become activated by an IL-1-dependent cascade of events. Our data supports the theory that stromelysin becomes bound to the cartilage in its latent form as the matrix is being assembled. This latent enzyme remains fixed to the scaffolding of the cartilage matrix, probably through a specific cellular matrix protein or receptor. Once activated by biochemical stimuli, stromelysin may produce significant degradation in articular cartilage in the absence of appropriate inhibitors.

Although the data presented below involves metalloproteases, alternative pathways, such as serine protease systems, play an important role in cartilage degradation. The cartilage powder assay system is a useful method for examining the mechanisms of these alternative degradation pathways, and is therefore not limited to the metalloprotease system, rather is applicable to all systems involving proteases.

To detect the activation of degradative enzymes (such as stromelysin) in the powder assay, a small amount of dry powder was weighed out and brought up in TBS so that the suspension contained 1 g of powder per 50 ml. The suspension was pipetted into 100 μl aliquots and placed into 1.5 ml centrifuge tubes. P-aminophenylmercuric acetate (APMA), a potent activator of stromelysin, was added to the tubes (15 μl per 100 μl suspension). The tubes were allowed to incubate in a 37° C. water bath for 18-24 hours. After incubation, the tubes were centrifuged, aliquots of the supernatant were taken and counted in a liquid scintillation counter to determine the amount of degradation that occurred (ie., the amount of [$^{35}$S]O$_4$ counts released from the pellet into the surrounding medium). The remaining contents of the tubes were digested in 250 μl of formic acid at 70° C. for 8 hours. The digested counts were then taken, and the percent of counts released was calculated for each sample:

% RELEASE =

$$\frac{\text{RADIOACTIVITY IN SUPERNATANT AT 24 H.}}{\text{TOTAL RADIOACTIVITY IN POWDER SUSPENSION AT 0 TIME}} \times 100$$

Calculation of the percent of counts released corrects for any small variation in total counts between tubes.

We detected a 3- to 4-fold increase in cartilage degradation in the triplicate samples exposed to APMA compared with the control samples. The results are depicted in the table below:

TABLE 1

| | % TOTAL COUNTS RELEASED |
|---|---|
| CONTROLS | 8.99% |
| | 8.89% |
| | 10.56% |
| Average | 9.48% |
| SUSPENSION + APMA | 36.73% |
| | 32.00% |
| | 32.64% |

TABLE 1-continued

| | % TOTAL COUNTS RELEASED |
|---|---|
| Average | 33.79% |

The results show for the first time using this procedure that proteases exist in a latent form, bound to the cartilage matrix. The thorough washings used in our assay preclude the likelihood that the degradation was due to adventitial proteases. Rather, the activator APMA converted latent stromelysin, bound to the matrix, into its active form, resulting in a marked increase in cartilage degradation.

In the powdered cartilage assay, labels other than a radioactive label, for example a dye, can be used to monitor inhibition or promotion of cartilage degradation. In this case, unlabeled powdered cartilage is obtained as described above. The cartilage is resuspended in a physiologic buffer and mixed with the test substance in the presence of a dye capable of binding to glycosaminoglycan components of the proteoglycans and producing a measurable color change when added to a solution containing glycosaminoglycans. A preferred dye is 1,9-dimethyl Methylene Blue, although other dyes, for example Safronin-O, Toluidine Blue, or Alcian Blue, can be used in the assay. Since degradation of cartilage results in release of glycosaminoglycans into the solution, the extent of the color change in the solution is therefore a measure of the extent of degradation of cartilage and can be quantitated in a spectrophotometer.

The assay of the invention offers many advantages over the existing live plug assay described by Dingle et al., 1979, Biochem. J. 184:177., and Treadwell et al., 1986, Arch. Biochem. Biophys. 251:715. The live plug assay involves obtaining cartilage plugs from bovine radio-carpal joints using a bore device, and then using a template plate to shave off the most superficial 1.5 mm layer of cartilage. These plugs are then placed in a $CO_2$ incubator at 35° C. with DMEM and [$^{35}$S]O$_4$ to radioactively label the proteoglycans in the matrix. After labeling, the plugs are then transferred to 96 well Falcon TM plates, each well containing DMEM and the factor (activator or inhibitor of degradation) to be tested. Aliquots are then taken after a specified incubation period in the $CO_2$ incubator and counted in a liquid scintillation counter. By examining the counts in the medium, investigators can determine the amount of degradation that takes place in each live cartilage plug.

The live plug assay has several drawbacks: First, the size of each cartilage plug varies, despite the use of a template to shave off the outer 1.5 mm thus incurring inherent inaccuracy in the assay. Second, the assay is extremely time consuming. Third, the risk of contamination by bacteria and fungi is somewhat high.

The advantages of the new powdered assay system are as follows:

Speed: Instead of having to obtain plugs and cut them up using a template, cartilage for the new assay is obtained by resecting chips, which can be immediately washed and incubated. Once the powder is made, it can be quickly brought up in medium and several assays may be run. Aliquots of supernatant can be taken within 24 hours and counted in a liquid scintillation counter or, depending upon the label, monitored in a spectrophotometer. Since the amount of substrate in each aliquot of suspension (powder + medium) is relatively uniform, the percent of total degradation may be quickly calculated from the scintillation counter or spectrophotometric data.

Reproducibility: One cartilage harvest can yield a large quantity of cartilage powder, which is unlabeled or uniformly labelled with radioisotope. This preparation of powder can be brought up in suspension and consistently pipetted into smaller aliquots for numerous experiments. The pipetting accuracy of the artisan determines the amount of error between aliquots: an ordinary artisan, skilled in the art, pipetting correctly and accurately, will incur a variability between tubes as low as 2-5%.

Convenience: Availability of human tissue is unpredictable. The live plug system mandates that the experiments be done at the time of tissue availability. The new powder system of the invention eliminates this problem by allowing the artisan to resect the cartilage and store it in frozen form for later use. Also, large quantities can be taken at one time (since resection is the most labor-intensive step of the assay) and stored either labeled or unlabeled.

No Contamination: In contrast to the live plug system, the new powder assay system is free from the risk of contamination by bacteria and fungi.

A Natural System: Like the live plug system, the new frozen powder system is also one step away from an in vivo system. All of the components of the cartilage matrix are present.

In that the powdered cartilage assay is a remarkably efficient and accurate system that streamlines the process of measuring cartilage-degrading proteases in cartilage and synovial fluid, and in which the action of a large number of factors (inhibitors and activators) related to cartilage degradation can be tested, large scale testing of factors can be accomplished if the assay is incorporated into a kit usable by an ordinary artisan, for example, a medical technician. A kit, such as that described below, comprising powdered cartilage, represents one clinical application of the cartilage powder system.

Where the powdered cartilage is to b used in the method wherein degradation is measured by means of a dye which binds to released glycosaminoglycans, the kit contains the following components: 1) Several tubes containing a 1 mg/tube of nonradioactive bovine (or human) articular cartilage powder, lyophilized to dryness. 2) Buffer A: A separate solution of physiologic buffer (20 mM Tris-Cl, 150 mM NaCl, 5 mM $CaCl_2$, 5 $\mu$M $ZnCl_2$, 0.02% $NaN_3$, pH 7.4). 3) Buffer B: A solution containing one of the dyes described above. 4) A color chart for comparing test results with standard color ranges that are directly related to the amounts of glycosaminoglycans released during cartilage matrix degradation. This color chart would also list spectrophometric values for each color value, for standardization and measurement purposes. 5) Directions for using the kit.

The kit is used by following these steps: Add 100 $\mu$l of Buffer A to a tube containing 1 mg of lyophilized cartilage powder. 2) Add 1-100 $\mu$l of synovial fluid from a patient to the tube and incubate the mixture for 18-24 hours at room temperature, or at 37° C. 3) Centrifuge the tube at 5000 × g for 3 minutes. 4) Remove 10-20 $\mu$l of the supernatant (Buffer A + synovial fluid). 5) Add 0.5 ml of Buffer B to the supernatant mixture and look for a color change. The color intensity can be quantified either by visually comparing the color of the sample to the enclosed standard color chart, or by measuring the intensity of the color in a spectrophotometer.

The intensity of the color change is a direct measure of the amount of degradation that has occurred as a result of exposing the articular cartilage powder to the patient's synovial fluid. The condition of the patient's joint and extent of osteoarthritic change may be deduced from this result.

Where the kit contains lyophilized bovine articular cartilage radiolabeled with $[^{35}S]O_4$ instead of the unlabeled lyophilized powder mentioned above, buffer B and the standard color chart are excluded from the kit which is otherwise described above. Directions for using this kit are identical to the above kit for steps 1 through 4. Step 5 involves placing the sample in a scintillation vial, adding the appropriate volume of scintillation fluid, and measuring the amount of radioactivity in a liquid scintillation counter. The amount of radioactive label released from the proteoglycan groups in the cartilage matrix is indicative of the extent of cartilage degradation resulting from exposure of the matrix to the synovial fluid.

Normal synovial fluid exerts a chondroprotective effect on bovine articular cartilage; in contrast, bovine articular cartilage exposed to synovial fluid from an osteoarthritic knee joint undergoes significant amounts of degradation. Thus, in another application of the invention, synovial fluid and cartilage can be examined in order to identify the presence or absence of agents in either substance that act to promote or inhibit cartilage degradation.

For example, to identify natural molecules in synovial fluid that promote cartilage degradation, synovial fluid obtained from mammals that either do or do not have arthritis can be tested as follows: Synovial fluid can be mixed and incubated with proteins that have attached to them a dye such that if the proteins become degraded the dye is released into the liquid. The amount of dye released is directly related to the degree of degradation of the proteins, which in turn is related to the extent of protease activity in the synovial fluid. The amount of dye in the liquid is measured in a spectrophotometer. The results can be compared to control experiments wherein a buffer solution that does not contain proteases is incubated with dye-labeled proteins under the same conditions used for testing synovial fluid. Such dye labelled proteins for example, azocasein, azoalbumin and azocoll are available commercially.

Another method for identifying natural molecules that promote or inhibit cartilage degradation in synovial fluid obtained from mammals that either do or do not have arthritis involves testing the synovial fluid using the methods or kit described above. The presence or absence of substances that affect cartilage degradation can be determined by monitoring release of label when either whole or powered cartilage is prelabeled with $[^{35}S]O_4$, or by a color change when a dye is used. The results can be compared to results of control experiments, wherein the test substance is a buffer solution that has no effect on cartilage degradation. A decrease in the rate of degradation of cartilage compared to control values, indicates that the synovial fluid contains an inhibitor of cartilage degradation. Conversely, an increase in the rate of degradation of cartilage compared to control values, indicates that molecules that promote degradation of cartilage are present in the synovial fluid. Natural molecules so identified can be purified from synovial fluid. Molecules that inhibit cartilage degradation may prove to be of major therapeutical value in the treatment of arthritis. Molecules that promote cartilage degradation may be used to examine the mechanism(s) by which cartilage degradation occurs, which in turn may lead to improved therapies for the prevention of cartilage degradation.

Use of the methods or kit to examine synovial fluid for the presence or absence of agents that affect cartilage degradation also provides a valuable tool for the diagnosis of arthritis in a mammal. In disease states, the synovial fluid may be missing inhibitory or chondroprotective agents, or may contain aberrant levels of agents, namely proteases, that promote cartilage degradation. For example, synovial fluid obtained from a mammal suspected of having arthritis can be tested as described above. An increase in protease activity or in degradation of cartilage compared to control values, can be used as an indication that the mammal has arthritis. Similarly, synovial fluid obtained from individuals at risk (i.e., individuals whose families have a high incidence of osteoarthritis) can be tested using the methods or kit described above. Early detection of osteoarthritis may facilitate treatment of the individual with therapies designed to arrest or decrease the rate of cartilage degradation, and may therefore minimize the severity of the disease.

In yet another application of the invention, individuals that have arthritis can be monitored at frequent intervals to determine the severity of their disease. Synovial fluid can be obtained from such individuals and assayed using the methods or kit described above. An increase or decrease in cartilage degradation can be used as a measure of the progression of the disease. Individuals whose disease is progressing rapidly may then be treated more aggressively than those individuals whose disease is progressing more slowly.

The invention features yet other advantages as described below. Cartilage tissue, obtained through surgical or arthroscopic biopsy from an individual with arthritis can be examined for activity of various proteases in the cartilage matrix. The procedure involves taking the biopsy specimen and processing it to powdered form. The powder can then be suspended in a buffer solution and tested using the dye-labeled proteins described above, for the activity of such proteases. The results can be compared to those obtained using cartilage from an individual that does not have arthritis. Another example of an experiment to examine protease activity in powdered cartilage involves suspending the cartilage in a liquid and adding to that suspension a cocktail comprising radioactively labeled proteins and peptides, examples of which include bovine serum albumin, casein or other proteins that do not have any inherent protease activity. Following incubation of the cartilage with these proteins, trichloroacetic acid is added to the suspension to a final concentration of 10% such that high molecular weight proteins will be precipitated and smaller peptides will remain in solution. Precipitated proteins are separated from nonprecipitated proteins by filtration and the amount of label remaining in solution is measured in a liquid scintillation counter. The amount of label in the solution relates directly to the level of protease activity in the cartilage. Of the two methods just described, the former method is the preferred method because, in the latter method, release of proteoglycans from the cartilage may interfere with the trichloroacetic acid precipitation step. If cartilage from an individual with arthritis is found to contain elevated levels of proteases compared to control levels, such findings can be used a) to measure the severity or progression of the disease by periodically monitoring the levels of such enzymes; b) to design novel therapies to arrest the progression of the disease; and, c) as a research tool to examine the mechanism by which the disease progresses.

The assay of the invention can be used not only to test synovial fluid, but also other substances which potentially contain proteases or regulators of protease activity. Thus, other test substances include serum, urine, blister exudate, and bronchoalveolar lavage. Samples of the latter can be obtained from a mammal that either has or does not have emphysema, and tested in the assay. As described above for arthritic disease, the finding of proteases or regulators of protease activity in bronchoalveolar lavage may lead to a) the discovery of novel therapies for the treatment of emphysema, b) may provide a research tool to examine the mechanism by which the disease progresses, and c) may provide a method to measure the severity and progression of the disease, based on the levels of proteases or regulators.

What is claimed is:

1. A method for diagnosing arthritic disease with an inflammatory joint component involving protease activity in a mammal, said method comprising, mixing a sample of powdered cartilage obtained from said mammal with protein which is detectably labeled thereby forming a mixture wherein an amount of label is released from forming said mixture;

determining the amount of said label released from said protein, said amount being indicative of the level of protease activity in said sample; and comparing said level to a standard, wherein an elevated level of said protease activity in said sample is an indication that said mammal has said arthritic disease.

2. The method of claim 1 wherein said detectable label is a dye.

3. The method of claim 1 wherein said labeled protein is chosen from the group consisting of azocasein, azoalbumin, and azocoll.

4. The method of claim 1 wherein said protein is radioactively labeled.

5. A method for monitoring arthritic disease with an inflammatory joint component involving protease activity in a mammal, said method comprising, obtaining samples of synovial fluid from said mammal at least two time points;

mixing each of said samples with powdered cartilage, said cartilage being detectably labeled and suspended in liquid;

determining the amount of label released from mixing of said cartilage with each of said samples; and comparing said amount for each of said time points, wherein a difference in said amounts is indicative of the progression of said arthritic disease.

6. The method of claim 5 wherein the proteoglycan moieties of said powered cartilage are detectably labeled.

7. The method of claim 5 wherein said powered cartilage is labeled with [$^{35}$S]O$_4$.

8. The method of claim 10 wherein said dye is selected from the group consisting of 1,9-dimethyl Methylene Blue, Safronin-O Toluidine Blue, and Alcian.

9. A method for monitoring arthritic disease with an inflammatory joint component involving protease activity in a mammal, said method comprising, obtaining samples of powdered cartilage from said mammal at least two time points;

mixing each of said samples with protein which is detectably labeled;

determining the amount of said label released from mixing of said protein with each of said samples, said amount being indicative of the level of protease activity in each of said samples; and comparing said levels obtained at said time points, wherein a difference in said levels is indicative of the progression of said arthritic disease.

10. A method for monitoring arthritic disease with an inflammatory joint component in a mammal, said method comprising, obtaining samples of synovial fluid from said mammal at least two time points;

mixing each of said samples with powdered cartilage which is suspended in liquid in the presence of a dye capable of binding to glycosaminoglycan moieties released from said cartilage, wherein said dye undergoes a detectable change upon binding to said moieties;

measuring the detectable change produced by each of said samples as an indication of the level of protease activity in the samples; and comparing the detectable change produced by the samples as an indication of the progression of said arthritic disease.

* * * * *